United States Patent [19]

Cincotta et al.

[11] Patent Number: 5,741,503
[45] Date of Patent: Apr. 21, 1998

[54] METHOD FOR REGULATING METABOLISM WITH DOPAMINE BETA HYDROXYLASE INHIBITORS

[75] Inventors: Anthony H. Cincotta, Charlestown, Mass.; Albert H. Meier, Baton Rouge, La.; John M. Wilson, Charlestown, Mass.

[73] Assignees: The Board of Supervisors of Louisiana State University and Agricultural and Mechanical College, Baton Rouge, La.; Ergo Research Corporation, Wakefield, R.I.

[21] Appl. No.: 747,114

[22] Filed: Nov. 8, 1996

Related U.S. Application Data

[62] Division of Ser. No. 486,188, Jun. 7, 1995, Pat. No. 5,626,860.

[51] Int. Cl.$^6$ ........................................................... A61F 2/02
[52] U.S. Cl. ............................................. 424/423; 514/824
[58] Field of Search ............................. 424/423; 514/824

[56] References Cited

U.S. PATENT DOCUMENTS

| | | |
|---|---|---|
| 4,659,715 | 4/1987 | Meier et al. . |
| 4,749,709 | 6/1988 | Meier et al. . |
| 4,783,469 | 11/1988 | Meier et al. . |
| 5,006,526 | 4/1991 | Meier et al. . |

FOREIGN PATENT DOCUMENTS 2192541A  7/1988  United Kingdom .

OTHER PUBLICATIONS

Noma et al, Atherosclerosis 49:1 1983.
Barnett, Postgrad. Med. J., 56:11–14, 1980.
Burns et al., Int'l. Symp. on Chronopharm. and Chronother. Florida A&M Univ., pp. 315–381, 1978.
Cincotta et al., J. Endocrinol., 106:173–176, 1985.
Cincotta et al., Ann. Notr. Metab., 33:305–314, 1989.
Cincotta et al., Experimentia, 43:416–417, 1987.
Eiseman, J. Animal Science, 59;86–94, 1984.
Eiseman, J. Animal Science, 59:95–104, 1984.
Emata et al., J. Exp. Zool., 233:29–34, 1985.
Harel et al., Proc. La. Acad. Sci., 38:125, 1975.
Joseph et al., Proc. Soc. Exp. Bio. Med., 146:1150–1155, 1974.
Kodama et al., Diabetes Care, 13:1109–1111, 1990.
Komorowski et al., Aliment. Nutr. Metab., 1:293, 1980.
Larsson et al., La Kartidningen, 82:4425, 1985.
Martin et al., The Condor, 75:369–374, 1973.
Martin et al., Chronobiology, pp. 641–646, 1974.
Martin et al., Proc. La. Acad. Sci., 38:127, 1975.
Martin et al., Ame. Zool., 18:672, 1978.
Martin, Hormonal Regulation of Migratory Orientation ..., Diss. LSU, 1974.
Martin, Factors Influencing the Ciradian Rhythm . . . , Thesis Sam Houston State College, 1969.
Masukawa et al., Jpn. J. Pharmacol., 64:141–146, 1994.
Meier et al., Gen. and Comp. Endocrinol., 3:499–508, 1972.
Meier et al., Gen. and Comp. Endocrinol., 26:253–258, 1975.
Meier et al., Current Ornithology, 2:303–343, 1984.
Meier et al., Experientia, 48:248–253, 1992.
Meier et al., Gen. and Comp. Endocrinol., 17:311–318, 1971.
Meier et al., Proc. Soc. Exp. Bio. and Med., 137:408–415, 1971.
Meier et al., Science, 173:1240–1242, 1971.
Meier et al., Physiol. Zool., 41:95–103, 1968.
Palatini et al., Biochem. Pharm., 38:1011–1013, 1989.
Paolisso et al., J. of Human Hyper., 6:175–179, 1992.
Rett et al., Postgrad. Med J., 62:59–64, 1986.
Southern et al., J. Anim. Sci., 68:931–936, 1990.
Torlone et al., Diabetologia, 34:199–125, 1992.
Wilson et al., Chronobio. Int., 6;113–121, 1989.

*Primary Examiner*—Carlos Azpuru
*Attorney, Agent, or Firm*—Darby & Darby

[57] ABSTRACT

This invention relates to methods for regulating or ameliorating lipid metabolism which comprise administration or timed administration of inhibitors of dopamine beta hydroxylase (DBH).

16 Claims, 3 Drawing Sheets

METHOD FOR REGULATING METABOLISM WITH DOPAMINE BETA HYDROXYLASE INHIBITORS

This is a division of application Ser. No. 08/486,188, filed Jun. 7, 1995, now U.S. Pat. No. 5,626,860.

FIELD OF THE INVENTION

This invention relates to methods for regulating or ameliorating lipid and glucose metabolism. This invention, further, relates to methods for reducing in a subject, a vertebrate animal (including a human), at least one of the following indices of metabolism: body fat stores, insulin resistance, hyperinsulinemia, hyperglycemia, hyperlipidemia, elevated blood lipoproteins (such as triglycerides and cholesterol including chylomicrons, VLDL and LDL), and/or increasing in the subject the plasma HDL, and, more generally, the improvement of metabolism disorders, especially those associated with obesity, atherosclerosis and Type II diabetes. The methods comprise administration or timed administration (i.e. administration at a predetermined time within a 24-hour period) of inhibitors of dopamine beta hydroxylase (DBH).

BACKGROUND OF THE INVENTION

Obesity and Lipid Metabolism Disorders—Body Fat Loss

Figure 1:
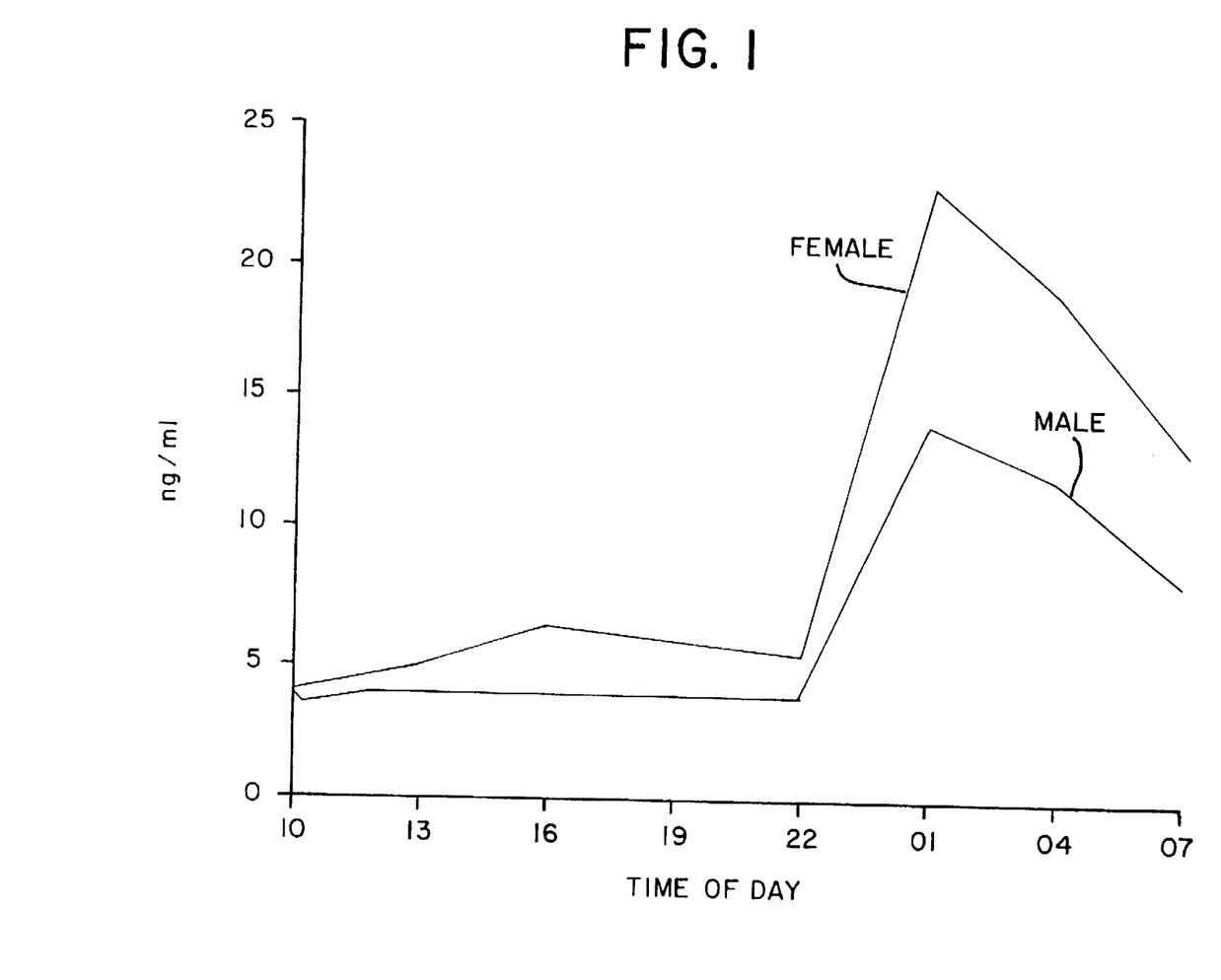
FIG. 1 depicts the standard prolactin profile for healthy young humans in terms of average prolactin values (ng/ml) vs time of day in hours. M=standard prolactin profile for males; F=standard prolactin profile for females.

In humans obesity can be defined as a body weight exceeding 20% of the desirable body weight for individuals of the same sex, height and frame (Salines, L. B., in *Endocrinology & Metabolism*, 2d Ed., McGraw-Hill, New York 1987, pp. 1203–1244; see also, R. H. Williams, *Textbook of Endocrinology*, 1974, pp. 904–916). In animals (including humans) obesity can additionally be defined by body weight patterns correlated with prolactin profiles given that members of a species that are young, lean and "healthy" (i.e., free of any disorders, not just metabolic disorders) have daily plasma prolactin level profiles that follow a regular pattern with little or no standard deviation. The "healthy" prolactin profile for humans (male and female) is depicted in FIG. 1.

Obesity, or excess fat deposits, correlates with and may trigger the onset of various lipid metabolism disorders, e.g. hypertension, Type II diabetes, atherosclerosis, etc.

Even in the absence of clinical obesity (according to the above definitions) the reduction of body fat stores (notably visceral fat stores) in humans, especially on a long-term or permanent basis, would be of significant benefit, both cosmetically and physiologically.

The reduction of body fat stores in domestic animals (including pets) especially on a long-term or permanent basis would also obviously be of considerable economic benefit to humans, particularly since farm animals supply, a major portion of a person's diet; and the animal fat may end up as de novo fat deposits in humans.

Whereas controlled diet and exercise can produce modest results in the reduction of body fat deposits, prior to the cumulative work of the present inventors (including the prior co-pending patent applications and issued U.S. patents referred to below), no truly effective or practical treatment had been found for controlling obesity or other lipid metabolism disorders that usually accompany obesity.

Elevated plasma concentrations of one or more of cholesterol- or triglyceride-carrying lipoproteins (such as chylomicrons, very low density lipoproteins (VLDL) and low-density lipoproteins (LDL) are considered abnormal when they exceed a well-established normal limit, generally defined as the ninety-fifth percentile of a random population. Elevated levels of these substances have been positively correlated with atherosclerosis and increased risk of cardiac infarction (i.e. heart attack) which is the leading cause of death in the United States. Strong clinical evidence has been presented in which a reduction in plasma concentration of these substances correlates with a reduced risk of atherosclerosis (Noma, A., et al., *Atherosclerosis* 49:1, 1983; Illingworth, D. and Conner, W., in *Endocrinology & Metabolism*, McGraw-Hill, New York 1987). Thus, a significant amount of research has been devoted to finding treatment methods which reduce elevated levels of plasma cholesterol and triglycerides.

Another subset of the plasma lipoproteins found in vertebrates are high density lipoproteins, or HDL. HDL serve to remove free cholesterol from the plasma. A high HDL concentration as a percentage of total plasma cholesterol has been associated with a reduced risk of atherosclerosis and heart disease. Thus, HDL are known in the lay press as "good" cholesterol. Therefore, therapeutic strategies involve attempts both to reduce plasma LDL and VLDL content (that is, reduce total plasma cholesterol), and to increase the HDL fraction of total plasma cholesterol. Several lines of research have indicated that simply increasing HDL is of benefit even in the absence of reducing LDL or VLDL concentration (Bell, G. P. et al., *Atherosclerosis* 36:47–54, 1980; Fears, R., *Biochem. Pharmacol.* 33:219–228, 1984; Thompson, G., Br. *Heart J.* 51:585–588, 1989; Blackburn, H. *N.E.J.M.* 309:426–428, 1983).

Current therapies for elevated lipid and lipoprotein values include a low fat diet and elimination of aggravating factors such as sedentary lifestyle. If the elevated lipid and lipoprotein levels are secondary (i.e. incident to e.g. a deficiency of lipoprotein lipase or LDL receptor, various endocrine pathologies, alcoholism, renal disorders, hepatic disorders) then control of the underlying disease is also central to treatment. Elevated blood lipid and lipoprotein levels are also treated with drugs, which usually alter the levels of particular components of the total plasma cholesterol, as well as reduce the total plasma lipid component. Among the most recently introduced drugs to treat such conditions is lovastatin (MEVACOR™) which selectively inhibits an enzyme involved in cholesterol production, 3-hydroxy-3-methylglutaryl coenzyme A (HMG-CoA) reductase. This drug specifically reduces total cholesterol and can cause a modest (5–10%) increase in HDL concentrations. However, benefit from this therapy varies from subject to subject.

Moreover, use of the HMG-CoA enzyme inhibitor is sometimes accompanied by side effects such as liver-toxicity, renal myoglobinuria, renal shutdown, and lenticular opacity. The risk of such side effects necessitates close monitoring of the patients (e.g., monthly liver function tests are required).

Another drug prescribed against elevated cholesterol and triglycerides is clofibrate. The effectiveness of clofibrate also varies from subject to subject and its use is often accompanied by such side effects as nephrotic syndromes, myalgia, nausea and abdominal pain.

DIABETES

Diabetes, one of the most insidious of the major diseases, can strike suddenly or lie undiagnosed for years while attacking the blood vessels and nerves. Diabetics, as a group, are far more often afflicted with blindness, heart disease, stroke, kidney disease, hearing loss, gangrene and impotence. One third of all visits to physicians are occasioned by this disease and its complications. Diabetes and its complications are a leading cause of premature death in the United States and in the Western world.

Diabetes adversely affects the way the body uses sugars and starches which, during digestion, are converted-into glucose. Insulin, a hormone produced by the pancreas, makes the glucose available to the body's cells for energy. In muscle, adipose (fat) and connective tissues, insulin facilitates the entry of glucose into the cells by an action on the cell membranes. In the liver the ingested glucose is normally converted to $CO_2$ and $H_2O$ (50%); to glycogen (5%); and to fat (30–40%), the latter being stored as fat deposits. Fatty acids from the adipose tissues are circulated, returned to the liver for re-synthesis of triacylglycerol and metabolized to ketone bodies for utilization by the tissues. The fatty acids are also metabolized by other organs.

The net effect of insulin is to promote the storage and use of carbohydrates, protein and fat. Insulin deficiency is a common and serious pathologic condition in humans. In insulin-dependent (IDDM or Type I) diabetes, wherein the pancreas produces little or no insulin, insulin must be injected daily. In noninsulin-dependent (NIDDM or Type II) diabetes the pancreas retains the ability to produce insulin, in fact it may produce higher than normal amounts of insulin (hyperinsulinemia), but due to a cellular resistance to insulin, the amount of insulin is relatively insufficient. Insulin resistance can be defined as a state in which a normal amount of insulin produces a subnormal biologic (metabolic) response. In insulin-treated patients with diabetes, insulin resistance is considered to be present whenever the therapeutic dose of insulin exceeds the secretory rate of insulin in normal persons. Insulin resistance is also associated with hyperinsulinemia when normal or elevated levels of blood glucose are co-present.

Either type of diabetes causes widespread metabolic abnormalities. In most NIDDM subjects, the metabolic abnormalities associated with NIDDM are (1) reduced entry of glucose into various "peripheral" tissues and (2) increased liberation of glucose into the circulation from the liver. Thus, there is an excess of extracellular glucose and a deficiency of intracellular glucose. Elevated blood lipids and lipoproteins are a further common complication of diabetes. The cumulative effect of these diabetes-associated abnormalities is severe damage to blood vessels and nerves.

There is, currently, no effective treatment for controlling either hyperinsulinemia or insulin resistance, except for certain work by the present inventors as follows:

PREVIOUS WORK OF THE PRESENT INVENTORS

The present inventors and their co-workers have found that administration of certain prolactin inhibitors (e.g., dopamine agonists such as bromocriptine) and/or prolactin stimulators (e.g., dopamine antagonists, such as metoclopramide; serotonin agonists and precursors, such as 5-hydroxytryptophan) and particularly administration of such substances at predetermined times, reduce body fat stores, obesity, plasma triglycerides and cholesterol and insulin resistance: U.S. Pat. Nos. 4,659,715; 4,749,709; 4,783,469; 5,006,526 5,344,832 and PCT application US 921/1166.

RELATED APPLICATIONS

Co-pending patent application Ser. No.07/192,332 (now abandoned in favor of its Rule 62 continuation Ser. No. 07/919,685) discloses methods for regulating lipid metabolism disorders by administering prolactin (or-both prolactin and a glucocorticosteroid ("GC")) into the bloodstream of an animal or human on a timed daily basis in an amount and for a period of time sufficient to increase insulin sensitivity.

The prolactin (or prolactin and glucocorticosteroid—"GC") injections are timed to create a peak in the subject's daily prolactin (or both prolactin and glucocorticosteroid) level profile that coincides in time with the peak prolactin level (or with both prolactin and GC peaks, respectively) of a lean, insulin-sensitive human in order to increase insulin sensitivity and reduce body fat stores. Alternatively, injections of the same agent(s) are timed towards the peak prolactin level time of an obese subject to achieve fat gain in a lean subject, if desired.

Co-pending application Ser. No. 07/463,327 (now abandoned in favor of its Rule 62 continuation 08/249,808 which is a continuation of Ser. No. 07/719,745, now U.S. Pat. No. 5,344,832) discloses a method of modifying and resetting prolactin and GC rhythms in an obese animal by administering a dopamine agonist at a predetermined time of day such that the prolactin (and/or GC) peak(s) of the obese animal will be phase-shifted to coincide with those of a lean animal. This results in the reduction of at least one of the following: body fat stores, body weight, hyperinsulinemia, hyperglycemia and the increase of insulin sensitivity.

In co-pending application Ser. No. 07/719,745 (now U.S. Pat. No. 5,344,832) discloses and claims enhanced methods for modifying and resetting the phase as well as the amplitude of prolactin daily rhythms. These methods comprise both (a) administering to the subject a dopamine agonist just after the time at which the normal prolactin profile peaks to reduce prolactin levels to the low "day" levels and (b) administering to the subject a prolactin stimulator at a time before the prolactin level peaks in normal subjects to achieve or maintain a peak for prolactin at night-time. The objective of this treatment is alteration of the subject's prolactin secretion profile to mimic in shape and time the profile of a lean healthy human not suffering from one or more of these metabolic disorders.

U.S. Pat. No. 5,344,832 also discloses and claims the further administration of a thyroid hormone to subjects that are being treated with a dopamine agonist and prolactin stimulator, especially to those subjects that are chronically or seasonally hypothyroid.

Co-pending applications Ser. No. 07/995,292 (which is a continuation-in-part of U.S. application Ser. No. 07/719,745, now U.S. Pat. No. 5,344,832) and Ser. No. 08/264,558 (which is a continuation-in-part of U.S. application Ser. Nos. 07/995,292, 08/178,569 and 08/171,897) discloses methods for determining whether the daily circulating prolactin profile in a subject is abnormal, and methods for normalizing prolactin profiles found to be aberrant. In pertinent part, the treatment method involves administration of a prolactin inhibitor no later than the time at which, during waking hours, the prolactin level in the subject is at its highest. The method may also involve administration of a prolactin stimulator timed to cause a peak of prolactin level to occur during night-time. The objective of this treatment is alteration ("sculpting") of the subject's prolactin profile to mimic or approach in shape and time the profile of a lean healthy human not suffering from any disorders.

Co-pending patent application Ser. No.08/263,607; continuation-in-part of co-pending application Ser. No. 07/995,292, which is itself a continuation-in-part of Ser. No. 07/719,745 (now U.S. Pat. No. 5,344,832), discloses methods for regulating lipid and glucose metabolism by the timed administration of pirenzepine, methyl scopolamine or another muscarinic (preferably M1) receptor antagonist alone or in combination with a prolactin inhibitor as a treatment for (i) diabetes, particularly Type II diabetes, and more generally glucose metabolism disorders that are associated with Type II diabetes; and (ii) obesity and more generally lipid metabolism disorders. This application further discloses maintaining therapy for a sufficient period of time to cause a resetting of the treated subject's prolactin daily rhythm resulting in continuing metabolic improvement after the cessation of therapy.

Co-pending patent application Ser. No.08/271,881 discloses method of adjusting the phase relationship between the circadian rhythms for prolactin and for one or more immune responses. The invention involves normalizing (or resetting) the circadian rhythm for prolactin of a subject in need of such treatment to resemble that of a young healthy subject. The invention, further, involves adjusting the prolactin circadian rhythm so that its phase and amplitude correlate with the immunologic responsiveness to prolactin thus exerting an amplifying effect on a predetermined aspect of the immune response.

OBJECTS OF THE INVENTION

The present invention has as objects to improve indices of metabolism by ameliorating one or more abnormal parameters such as those associated with obesity and diabetes.

A specific object of the invention is to reduce the body fat stores of a vertebrate animal, including a human, by administering at least one DBH inhibitor, preferably at a predetermined time.

Another object of the invention is to correct abnormalities in the glucose or lipid metabolism of a vertebrate animal, including humans, by administering a DBH inhibitor, preferably at a predetermined time. This administration is directed towards at least one of the following: decreasing hyperinsulinemia; decreasing insulin resistance; decreasing hyperglycemia; decreasing elevated levels of at least one blood lipoprotein; decreasing serum triglycerides; and increasing the ratio of high density lipoproteins to low density lipoproteins.

A further object of the invention is to treat diabetes in a vertebrate animal, including a human, by administering a DBH inhibitor, preferably at a predetermined time. This administration is directed towards at least one of the following: reducing hyperinsulinemia; decreasing insulin resistance; and decreasing hyperglycemia.

Yet another object of the invention is a method to treat atherosclerosis in a vertebrate animal, including humans, by administering a DBH inhibitor, preferably at a predetermined time. This administration is directed towards at least one of the following: decreasing elevated levels of one or more blood lipoproteins; decreasing serum triglycerides.

In addition, another object of the invention is continuing the administration of a DBH inhibitor for such a time period as to reset the central neural oscillators (e.g. those expressed by the circadian rhythm of circulating prolactin) such that their phase and amplitude (e.g. the phase and amplitude of the prolactin rhythm) approaches that of a lean and healthy subject of the same species (and where applicable sex), this effect persisting even after the cessation of the administration of the DBH inhibitor.

SUMMARY OF THE INVENTION

At least one of the foregoing objects is accomplished by:

(a) A method that involves administration to a vertebrate subject in need of such treatment, fusaric acid or another DBH inhibitor in an amount effective to improve one or more aberrant indices associated with lipid metabolism disorders (e.g., obesity, high cholesterol, and elevated levels of other blood lipids and lipoproteins).

(b) Another method that involves administration to a vertebrate subject in need of such treatment, fusaric acid or another DBH inhibitor in an amount effective to improve one or more aberrant indices associated with glucose metabolism disorders (e.g., glucose intolerance, insulin resistance, hyperglycemia, hyperinsulinemia and Type II diabetes) and/or with lipid metabolism disorders (e.g. obesity, hyperlipidemia, hypercholesterolemia).

Preferably, administration of the DBH inhibitor in (a) or (b) above is to occur at a predetermined time ("timed administration") during a 24-hour period to augment its beneficial effect.

Continuing the timed therapies referred to above for a period of time stabilizes these improvements and often causes them to persist after cessation of the treatment. Persistence and stabilization of these improvements and resetting of circadian rhythms is referred to as the "indirect effect" or "long-term effect" of DBH inhibitors (alone or in combination with prolactin inhibitors), and is attributed to resetting of a hypothalamic metabolistat expressed by way of circadian rhythms, more specifically prolactin rhythms and neural phase oscillators in the central nervous system. These effects can persist on a long-term basis after cessation of treatment.

As used herein, the term "DBH inhibitor" shall include compounds having this property as well as prodrugs and metabolites thereof in free form or as pharmaceutically acceptable salts. As used herein "prodrug" means a compound which, once administered to a host, is converted into a DBH-inhibiting compound disclosed herein or into a DBH-inhibiting metabolite thereof. A "metabolite" of a compound disclosed herein is an active derivative of a compound disclosed herein which is formed when the compound is metabolized.

DETAILED DESCRIPTION OF THE PREFERRED EMBODIMENTS

All patents, patent applications and literature references cited herein are incorporated by reference in their entirety as if their disclosures were physically present in the present specification. In case of conflict, however, the present disclosure controls.

Vertebrate animals include without limitation humans, other mammals (e.g. domestic animals, laboratory animals and pets) and birds.

Although not wishing to be bound by theory, the present inventors believe that fusaric acid and other DBH inhibitors have the ability to regulate and ameliorate lipid and glucose metabolism via a mode of action (i.e. a mechanism or pathway) that is different from that of D2 dopamine agonists or M1 muscarinic receptor antagonists.

TIMED ADMINISTRATION FOR ALTERING LIPID AND GLUCOSE METABOLISM

The direct effect of fusaric acid or other DBH inhibitors in accomplishing one or more of the following: reducing body fat stores, reducing blood lipids, reducing blood lipoproteins (LDL, VLDL and chylomicrons) and increasing HDL/LDL ratio, can be effected by administering to a vertebrate animal in need of such treatment from about 1 to about 150 mg/kg of body weight per day and preferably 5 to 100 mg/kg of body weight per day of fusaric acid.

Non limiting examples of DBH inhibitors that are preferred for use in practicing the present invention are fusaric acid, disulfiram, 3-phenylpropargylamine and 5-(4'-chlorobutyl)-picolinic acid.

The maximum dose of fusaric acid in humans is anticipated at about 2000 mg/patient/day.

If disulfiram is used, the general dose is from about 50 to about 700 mg/kg of body weight per day with 100-500 mg/kg being preferred. The anticipated maximum dose for humans is about 1200 mg/patient/day.

If 3-phenylpropargylamine is used, the general dose is from about 10 to about 150 mg/kg of body weight per day with 20-40 mg/kg of body weight per day being preferred. The anticipated maximum dose for humans is about 5 g/patient/day.

If 5-(4'-chlorobutyl)-picolinic acid is used as the DBH inhibitor the general dosage range is between about 10 and 200 mg/kg of body weight per day. The preferred dosage range is between about 20 and 40 mg/kg of body weight/day.

Other DBH inhibitors with similar pharmacokinetic properties are anticipated to be used at comparable amounts on a molar basis. The amounts of other DBH inhibitors will have to be adjusted as is well-known in the art based on their individual pharmacokinetic properties (See, e.g., Benet et al, 1990, *Pharmacokinetics: The Dynamics of Drug Absorption, Distribution and Elimination* in Gilman et al Eds, the Pharmacological Basis of Therapeutics, Pergamon Press, N.Y.). Furthermore, it is expected that the amount of each compound will be subject to optimization but that this will involve no more than routine experimentation.

Other DBH inhibitors that can be used in the practice of the invention include without limitation diethyldithiocarbamate, beta-chlorophenethylamine, 4-hydroxybenzylcyanide,2-halo-3-(p-hydroxyphenyl)-1-propene,1-phenyl-1-propyne, 2-phenylallylamine, 2-(2-thienyl)allylamine and derivatives thereof such as 2-thiophene-2-(2-thienyl)allylamine, 3-phenylpropargylamine, 1-phenyl-1(aminoethyl)ethene and derivatives thereof such as N-(trifluoroacetyl)phenyl-1 (aminoethyl) ethene and 5-picolinic acid derivatives, such as 5-(4'-chlorobutyl)-picolinic acid and other 5-picolinic acids similarly alkyl- or haloalkyl-substituted, e.g., with $C_1$–$C_6$ alkyl groups optionally themselves substituted with one or more halogen atoms.

As used herein, DBH inhibition (or inhibiting DBH, or reducing DBH activity) refers to reducing the "in vivo" activity of the enzyme DBH by at least about 10%.

One preferred embodiment involves administering a sufficient amount of a DBH inhibitor of the present invention to inhibit DBH to a subject in order to regulate or ameliorate glucose or lipid metabolism. The effective amount to inhibit DBH (or the DBH inhibition dosage range) for the DBH inhibitors of the invention is available in the literature or may be readily ascertained by administering increasing levels of the subject DBH inhibitor to a patient until DBH inhibition (as measured by analysis of the patient's serum) occurs.

The effective amount (or dose) of fusaric acid for achieving 10% inhibition of DBH in humans is between about 0.7 and 1.5 mg/kg of body weight per day.

It is preferred that a DBH inhibitor be administered at a predetermined time during a 24-hour period designed to reduce lipogenesis most preferably during a daily lipogenic interval when most of the fat is synthesized. The interval is determined indirectly by measuring one or more plasma lipid values, preferably VLDL values at several (e.g. 3 or 4) spaced-apart times within all or a portion of a 24-hour period and determining the interval when the circulating VLDL increases, reaches a maximum and then begins to decline. In general, the interval of increased lipogenesis precedes in phase the interval of increased VLDL and occurs during the latter half of the subject's daily activity period (for humans, usually in early evening). However, it is preferred to make the aforedescribed measurements, rather than rely on the general rule because of the possible shifts of this interval in subjects in need of treatment.

For example, the DBH inhibitor might be administered about 6–12 hours before the increase in VLDL values, or at the beginning of the daily activity/wakefulness period. Because timing of the administration will vary with the species to be treated (diurnal/nocturnal) and dosage and half-life of the DBH inhibitor, the foregoing 6–12 hour interval can serve as a guideline for more precise determinations. Effectiveness of the administration at a particular time is assessed by such indices as triglyceride level, body fat, cholesterol level, VLDL level etc.

Alternatively, the DBH inhibitor can be administered at the beginning of the daily activity period of the subject, (in humans within the interval 0700 to 1300) and the same indices can be measured only to assess effectiveness of the treatment (i.e. the determination of the lipogenesis interval as such can be omitted).

Glucose metabolism can also be altered, by the administration of a DBH inhibitor, preferably by the "timed" administration thereof, and symptoms associated with type II diabetes can thus be decreased or eliminated. Instead of lipid values, one or more appropriate indices for glucose metabolism and/or type II diabetes should be measured (e.g. glucose tolerance, glucose level, insulin level, insulin sensitivity, glycosylated hemoglobin) to determine an interval of increased glucose production and/or to assess effectiveness of the treatment. The amounts and timing of DBH inhibitors to treat glucose metabolism disorders are generally the same as above.

In more detail, a preferred effective time for administering a DBH inhibitor is first identified. This can be accomplished by routine experiment as described below, using one or more groups of animals (preferably at least 5 animals per group).

In animals, lipogenic inhibition by DBH inhibitor treatment can be assessed by administering the inhibitor at a particular time of day and determining the effect of the administration (if any) by measuring one or more indices associated with lipogenesis (Meier, A. H., *Am. J. Physiol.*, supra, 1977 or Cincotta, A. H. et al *Horm. Metabol. Res.*, supra, 1989), and comparing the post-treatment values of these indices to the values of the same indices prior to treatment. A convenient first time for administering the DBH inhibitor is towards the beginning of the daily activity period of the host.

If the time chosen is sufficiently effective in decreasing lipid metabolism indices, the experimentation can stop. If the results of the administration are not satisfactory, then the appropriate time of administration is adjusted as follows: The DBH inhibitor can be administered to the same (or preferably another) group of animals at a different time of day and the same indices can be measured, and compared to the first set of lipogenic index values and/or to a pretreatment set of lipogenic index variables. The second test time of administration is preferably 6–12 hours earlier (or later) than the first test administration time. Based on the difference in index values, the second test time can be selected as the time of therapy, or another (third) test time of administration can be selected by interpolation (or extrapolation). For example, if a third time were selected in Example 2 or 3 it could have been around 1400 h. At most, this time-ascertaining experiment would need to be conducted four times. The duration of each test treatment is 2–14 days.

The same procedure can be followed for determining a preferred effective time of administration for affecting glucose metabolism, i.e. a time of administration during the glucose metabolism responsiveness "window" or "interval". The present inventors have also found that DBH inhibitors have more pronounced beneficial effects on aberrant glucose metabolism if administered at certain predetermined times (which may but need not be the same as the preferred times for altering lipid metabolism) during a 24-hour period. Again, a first test time of administration is selected and a test administration is conducted for 2–14 days. If the result is not satisfactory (based on comparison of the values of pretreatment and post-treatment glucose metabolic indices) a second administration time is selected (and optionally a second group of animals is tested), and so on as described above for treatment of lipid metabolism aberrations.

The approach for determining a preferred effective time of administration in a human is basically the same: a DBH inhibitor is administered daily to a human in need of lipid (or glucose) metabolism modification at a first time of day (e.g. at 07:00 h) for 2–14 days, preferably a week. The relevant metabolic indices are measured prior to, during, and after treatment. Measurement of these indices is preferably made at the same time of day (between 14:00 and 22:00).

If the treatment selected is effective, the time of the test administration is adopted as the time of treatment for the human.

If the time selected is not sufficiently effective (i.e. produces no significant change, or produces an adverse change in the relevant metabolic parameter or parameters) then administration at this time is immediately discontinued and a different time is selected (6–12 hours before or after the first time). The test treatment and metabolic index measurement is then repeated.

It should be noted that the time of light onset and duration of daylight as well as the age, sex and physical condition and the activity/rest regimen of the subject to be treated will influence the time or times at which administration of DBH inhibitor will be effective. It is thus most preferred to ascertain an effective administration time for each individual, using the above-described method. This is particularly true of humans who have diverse daily timetables.

The amount of fusaric acid (or other DBH inhibitor) to be used depends in part on the duration of the increased lipid metabolism responsiveness (or glucose metabolism responsiveness) interval or window and in part on the half-life of the compound used. For example fusaric acid has a half-life of about 8–9 hours and therefore the foregoing amount range is selected from about 1 to about 150 mg/kg.

The half-life for 3-phenylpropargylamine and for 5-(4[1]chlorobutyl)-piccolinic acid is about 6 hours.

The precise time of administration and/or amount of DBH inhibitor that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

While the subject is being treated, lipid or glucose metabolism is monitored by measuring one or more of the relevant indices at predetermined times during a 24-hour period. Treatment (amounts, times of administration and type of medication) may be adjusted (optimized) according to the results of such monitoring. The patient (or other subject) is periodically reevaluated to determine extent of improvement by measuring the same parameters, the first such reevaluation typically occurring at the end of four weeks from the onset of therapy, and subsequent reevaluations occurring every 4 to 8 weeks during therapy and then every 3 months thereafter. Therapy may continue for several months or even years with six months to one year being a typical length of therapy for humans. Some patients (e.g. patients in particularly poor physical condition, or those of an advanced age) may require a longer, or even continuous, treatment with a DBH inhibitor.

Adjustments to the amount(s) of drug(s) administered and possibly to the time of administration may be made based on these reevaluations. For example, if after 4 weeks of treatment one of the metabolic indices has not improved but at least one other index has, the dose could be increased by ⅓ without changing the time of administration.

Adjustments will be further modified and fine-tuned on an individual basis and with reference to the pharmacokinetics of the agent used.

In most cases, adjustment of timing and amount of drug(s) is not considered necessary if the results (i.e. amelioration of the metabolism disorder or disorders involved) are positive, i.e. if a clinically significant improvement has been achieved.

In treating non human vertebrates, generally, dosages within the aforementioned range of one or more DBH inhibitors, respectively, are each given, typically over a period ranging from about 10 days to about 180 days. Longer treatment times are possible when a benefit is obtained.

In the practice of this invention, a DBH inhibitor is administered daily to a subject preferably orally, or by subcutaneous, intravenous or intramuscular injection. Dermal delivery systems e.g., skin patches, as well as suppositories and other well-known systems for administration of pharmaceutical agents such as by inhalation of an atomized solution can also be employed.

Timed treatment with a DBH inhibitor can have the added benefit of decreasing cholesterol levels, while increasing HDL levels. As discussed above, such an alteration is highly desirable to reduce the risk of a subject to the development of atherosclerosis and subsequent heart disease.

Suitable DBH inhibitors include substances that directly or indirectly block dopamine beta hydroxylase. Nonlimiting examples include those given above, all of which are commercially available. The dosages of such DBH inhibitors, generally, will be subject to optimization as outlined above. Dosage optimization may be necessary independent of whether administration is timed by reference to the interval of increased lipogenesis or not.

LONG-TERM EFFECTS

Another aspect of the invention is directed to administration of a DBH inhibitor (e.g. fusaric acid) to produce long-term, lasting, or even permanent effects on lipid and/or glucose metabolism by-the administration of timed daily dosages to a vertebrate, animal or human, of a DBH inhibitor. The dosages are continued on a daily basis for a period sufficient to cause the beneficial effects on lipid and/or glucose metabolism to persist. This amounts to resetting the phase of at least one major neuroendocrine circadian rhythm (e.g., the central neural oscillator expressed by the circadian rhythm of circulatory prolactin) in the subject being treated, in that the phase and amplitude of the prolactin rhythm is modified to resemble that for a healthy, lean, young subject of the same species (and, if applicable, of the same sex), i.e. moves closer to that depicted in FIG. 1. This change in phase and amplitude can be assessed by comparison of the pre-treatment prolactin values at various times of the day before and after treatment. (See, e.g., application Ser. Nos. 07/995, 292 or 08/264,558.) The interval of increased lipogenic activity (or increased glucogenesis) of the subject can thus be related to the prolactin level daily rhythm of the subject. Essentially, any change in secretion, or blood level, of any hormone or other phenomenon which occurs in a circadian pattern and constitutes an expression of a central neural oscillation can be used to monitor alterations in the central neural oscillation it expresses.

Examples include prolactin, cortisol, thyrotropin, insulin, and body temperature without limitation. Resetting of circadian rhythms occurs if the administration of the DBH inhibitor (at a predetermined time) is continued for a period of time, generally at least about 10 days, preferably several months (e.g. typically 6 months for humans). Resetting has occurred if the beneficial effect(s) on the glucose/lipid metabolism persist on a long-term basis (e.g. months or even years) after the drug(s) is (are) discontinued. The foregoing amount, ranges and times of administration are the same as above. The doses of the inhibitor can be adjusted according to the results they produce in the terms of lipid values (or glucose metabolism indices), as described above.

These and other features of the invention will be better understood by reference to the experiments described in the examples below. In the examples the terminology "LD" refers to the light/dark cycle, the first number following the expression LD refers to the hours of light, and the second to the hours of darkness in the cycle. Thus, LD 14:10 refers to a cycle having 14 hours of light and 10 hours of darkness, and the period of a day is expressed in terms of 2400 hours. "BW" designates body weight, g represents grams, and mg represents milligrams.

All reagents and materials are commercially available. It should be noted that the Sprague-Dawley rat is a good, reliable model for both obesity and insulin resistance conditions in humans.

EXAMPLE 1

Effects of Ad Libitum Fusaric Acid Administration on Various Metabolic Indices in Male Sprague-Dawley Rat Eighteen male Sprague-Dawley rats (7.5 months of age) were provided either untreated rodent chow (Purina) or fusaric acid treated chow (5 mg/Kg B.W./day, Sigma Chemical, St. Louis) ad libitum for 2 weeks. Eighteen days after the last day of treatment blood samples were taken every eight hours over a twenty-four hour period beginning at the onset of light (0700, LD 12:12) in order to obtain overall daily mean concentrations of the parameters measured. The rats were fasted six hours prior to blood sampling, sacrifice and retroperitoneal fat measurement. Plasma triglycerides, total cholesterol, and glucose concentrations were determined utilizing diagnostic kits obtained from Sigma. Plasma cholesterol concentration was determined, after phosphogentisic acid precipitation of other lipoproteins, utilizing a kit obtained from Sigma. Plasma insulin concentration was determined utilizing a double-antibody radioimmunoassay kit obtained from ICN Biochemicals (Irvine, Calif.). Food consumption was monitored at regular 3-day intervals throughout the study.

TABLE 1

Effect of Ad-Libitum Fusaric Acid Administration on Retroperitoneal Body Fat and Various Metabolic Indices

| | Control | Fusaric Acid |
|---|---|---|
| Retroper. fat (g) | $3.75 \pm 0.18^{1,2}$ | $2.33 \pm 0.07^a$ |
| Pl. Triglyceride (mg/dL) | $199 \pm 15$ | $118 \pm 8^a$ |
| Pl. Cholesterol (mg/dL) | $107 \pm 6$ | $109 \pm 7$ |
| Pl. Glucose (mg/mL) | $214 \pm 8$ | $140 \pm 6^a$ |
| Pl. Insulin (µU/mL) | $189 \pm 8$ | $101 \pm 10^a$ |

[1]Mean ± standard error of the mean (n = 9/group).
[2]Food consumption was not significantly different between groups.
[a]Differs significantly from control (P < 0.05).

Fusaric acid treatment resulted in significant reductions of retroperitoneal fat (38%), as well as of plasma concentrations of triglycerides (41%), glucose (35%), and insulin (47%) (TABLE 1). These reductions represent significant improvements in lipid and glucose metabolism (i.e., reduction in insulin resistance) that persist long after treatment is discontinued.

EXAMPLE 2

Effects of Timed Fusaric Acid Administration on Various Metabolic Indices in Male Sprague-Dawley Rat Thirty-four male Sprague-Dawley rats (9 months of age) were divided into 3 groups of 11–12 rats each. Two groups were provided an oral dose of fusaric acid (5 mg/Kg B.W. in 1 mL of peanut butter) at either the onset or offset of light (LD 12:12, lights on 0700). A 1 ml dose of peanut butter only was given at the alternative time of day. A control group received 1 ml of peanut butter at both times (onset and offset of light). Rat chow (Purina) was made available to all groups ad libitum. Rats were treated for 2 weeks. Nineteen days after the last day of treatment 7–8 animals from each group were randomly selected for blood sampling and fat measurements (retroperitoneal and epididymal). As described in Example 1, 2–3 animals from each group were sacrificed every 8 hours beginning at the onset of light. All animals were fasted 6 hours prior to blood sampling and sacrifice. Plasma triglyceride, total cholesterol, glucose, and insulin concentrations were measured as described in Example 1.

TABLE 2

Effect of Timed Fusaric Acid Administration on Fat Stores and Various Metabolic Indices in the Male Sprague-Dawley Rat

|  | Control | Fusaric Acid (0700) | Fusaric Acid (1900) |
| --- | --- | --- | --- |
| Retroper. fat (g) | $4.63 \pm 0.27^{1,2}$ | $3.19 \pm 0.50^a$ | $3.18 \pm 0.50^a$ |
| Epididymal fat (g) | $7.47 \pm 0.44$ | $5.16 \pm 0.57^a$ | $5.67 \pm 0.50^a$ |
| Pl. Triglyceride (mg/dL) | $149 \pm 22$ | $104 \pm 23$ | $113 \pm 9^a$ |
| Pl. Cholesterol (mg/dL) | $172 \pm 10$ | $175 \pm 12$ | $132 \pm 23^{a,b}$ |
| Pl. Glucose (mg/dL) | $159 \pm 6$ | $160 \pm 12$ | $108 \pm 14^{a,b}$ |
| Pl. Insulin (μU/mL) | $178 \pm 11$ | $157 \pm 9$ | $113 \pm 5^{a,b}$ |

[1]Mean ± standard error of the mean (n = 7-8/group).
[2]Food consumption did not differ significantly between groups.
[a]Differs significantly from control (P < 0.05).
[b]Differs significantly from 0700 administration time.

The experiment reported in this Example was designed to test for differences in the effectiveness of fusaric acid based on time of administration. Times were selected to target fusaric acid treatment either toward (1900) or away (0700) from the peak interval of lipogenic and glycogenic activity in the healthy Sprague-Dawley rat.

Both times of fusaric acid treatment were equally effective in producing significant reductions in retroperitoneal and epididymal fat stores (both were decreased approximately 30%) (TABLE 2). However, only the 1900 h administration time significantly reduced plasma cholesterol, glucose and insulin concentrations compared to both the control and the 0700 h administration.

These results underscore the additional benefit of appropriate timing in the administration of fusaric acid. Only the 1900 time simultaneously reduced body fat stores in conjunction with reductions in indices associated with non-insulin dependent diabetes mellitus.

EXAMPLE 3

Indirect (Long-Term) Effect of Timed Fusaric Acid Administration on Metabolic Indices 3 Months After Cessation of Treatment Three months after cessation of fusaric acid treatment, blood samples were taken from the remaining 4 animals in control and treatment groups described in Example 2. Blood samples were taken over a twenty-four hour period in order to obtain overall mean daily concentrations of plasma triglyceride, cholesterol, glucose and insulin. All measurements were made according to the methodologies described in Example 1.

TABLE 3

Effects of Fusaric Acid Administration on Metabolic Indices 3 Months After Cessation of Treatment

|  | Control | Fusaric Acid (0700) | Fusaric Acid (1900) |
| --- | --- | --- | --- |
| Pl. Triglyceride (mg/dL) | $164 \pm 4^1$ | $180 \pm 7$ | $117 \pm 10^{a,b}$ |
| Pl. Cholesterol (mg/dL) | $162 \pm 4$ | $186 \pm 5^a$ | $139 \pm 6^{a,b}$ |
| Pl. Insulin (μU/mL) | $165 \pm 10$ | $143 \pm 6$ | $107 \pm 6^{a,b}$ |

[1]Mean ± standard error of the mean (n = 4/group).
[a]Differs significantly from control (P < 0.05).
[b]Differs significantly from 0700 group (P < 0.05).

Three months after cessation of treatment, plasma triglyceride, cholesterol, and insulin concentrations were still significantly reduced in the 1900 fusaric acid treatment group compared with either the control or the 0700 group (p<0.05). In fact, plasma values for these parameters (1900 group) were not significantly different from those obtained only 2.5 weeks after treatment. The 0700 h fusaric acid treatment, however did not lower triglyceride, cholesterol, or insulin levels compared with the controls.

3.5 months after cessation of treatment, blood samples were again taken from individuals rats in control (n=3) and fusaric acid treated (0700, n=4; 1900, n=4) rats for the determination of plasma prolactin concentrations. Samples were taken by orbital sinus puncture beginning at the onset of light (0700) and continuing every 4 hours thereafter over a 24 hour period. Plasma prolactin was measured utilizing an antibody and a rat prolactin standard supplied by the National Pituitary Program.

Figure 2A:
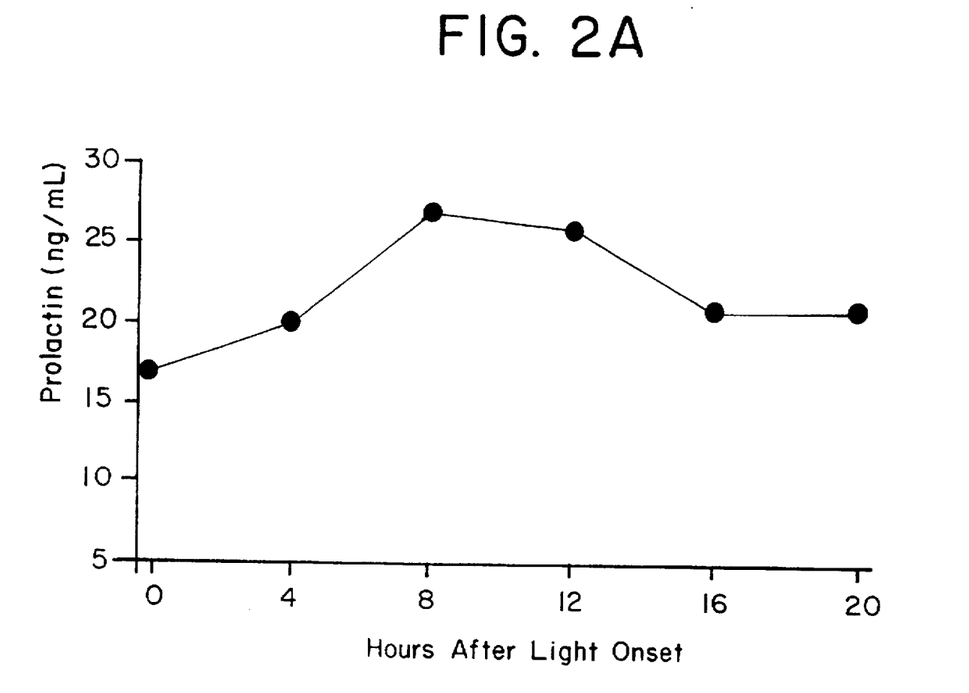
FIG. 2A depicts the daily plasma prolactin rhythm in rats treated with fusaric acid at 0700 h.
Figure 2B:
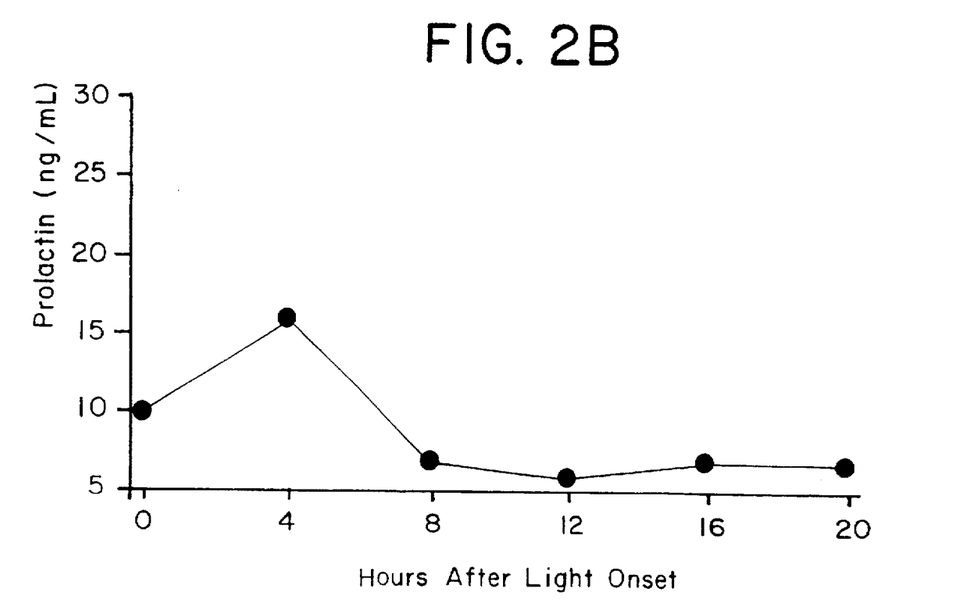
FIG. 2B depicts the daily plasma prolactin rhythm in rats treated with fusaric acid at 1900 h.
Figure 2C:
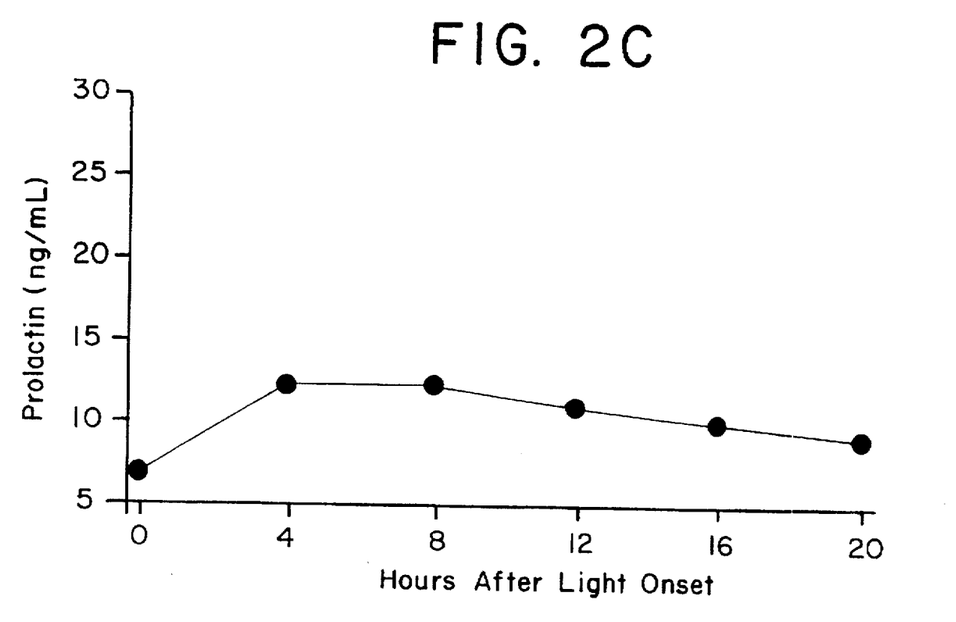
FIG. 2C depicts the daily plasma prolactin rhythm in untreated young (8 week old) rats.
Figure 2D:
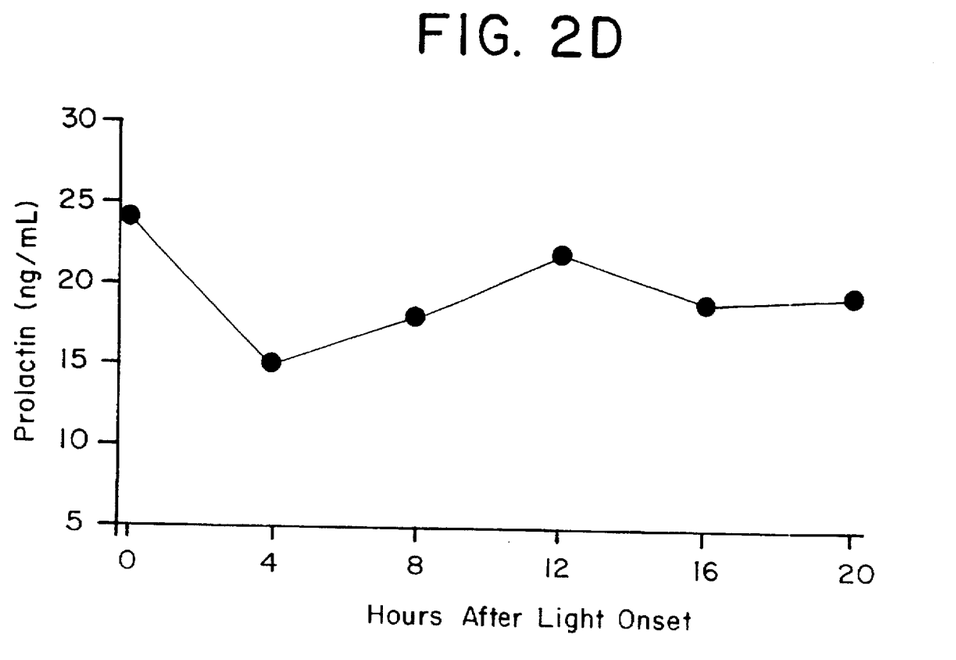
FIG. 2D depicts the daily plasma prolactin rhythm in untreated 50 week old rats.

3.5 months after treatment overall mean prolactin levels in the 1900 treated group (8.3 ng/mL; FIG. 2b) were significantly lowered compared to the controls (22 ng/mL; FIG. 2d) and similar to the prolactin levels of young, healthy, 8-week old rats that are lean and insulin sensitive (9.2 ng/mL; FIG. 2c). The prolactin levels in the 0700 treated group (19.8 ng/mL; FIG. 2a) were similar to those of 50-week old insulin-resistant controls (22 ng/mL).

Furthermore, the prolactin profile of the 1900 treated group approached the profile of young, lean, insulin-sensitive rats even though at the time of the prolactin test the members of the treated 1900 group were 50 weeks old. This experiment provides evidence that fusaric acid administered at the appropriate time adjusts prolactin profile to a profile approaching that of a young healthy individual and resets prolactin rhythm, in that the favorably modified profile persists for a considerable period of time after cessation of the timed treatment with fusaric acid.

These effects of properly timed fusaric acid treatment demonstrate long-term improvements in metabolic conditions associated with non-insulin dependent diabetes mellitus that persist long after the cessation of treatment.

The invention was described above with reference to preferred embodiments. In light of this description, however, it will be apparent to those skilled in the art that many omissions, additions and modifications are possible, all within the scope of the following claims.

What is claimed is:

1. A method for modifying lipid metabolism in a vertebrate animal or human subject in need of such treatment which comprises administering to said animal or said human at a predetermined time an effective amount for inhibiting dopamine beta hydroxylase activity in said animal or human of a compound having the property of inhibiting dopamine beta hydroxylase.

2. The method of claim 1 which comprises administering said dopamine beta hydroxylase inhibitor compound to reduce body fat stores.

3. The method of claim 1 which comprises administering said dopamine beta hydroxylase inhibitor compound to increase plasma HDL.

4. The method of claim 1 which comprises administering said dopamine beta hydroxylase inhibitor compound to reduce hyperlipidemia.

5. The method of claim 1 which comprises administering said dopamine beta hydroxylase inhibitor compound to reduce elevated blood lipoproteins.

6. The method of claim 1 wherein said predetermined time is the beginning of the daily activity period of the subject.

7. The method of claim 1 wherein said compound having the property of inhibiting dopamine beta hydroxylase is a member selected from the group consisting of fusaric acid, disulfiram, diethyidithiocarbamate, beta-chlorophenethylamine, 4-hydroxybenzyl cyanide, 2-halo-3-(p-hydroxyphenyl)-1-propene, 1-phenyl-1-propyne, 2-phenylallylamine, 2-(2-thienyl)allylamine, 2-thiophene-2-(2-thienyl)allylamine, 3-phenylpropargylamine, 1-phenyl-1-(aminoethyl)ethene, N-(trifluoroacetyl)phenyl(aminoethyl) ethene, 5-picolinic acid substituted with an alkyl group containing up to 6 carbon atoms, 5-picolinic acid substituted with a halo alkyl group containing up to 6 carbon atoms, prodrugs thereof, metabolites thereof, and pharmaceutically acceptable salts thereof.

8. The method of claim 7 wherein said dopamine beta hydroxylase inhibitor compound is 5-(4'-chlorobutyl) picolinic acid.

9. The method of claim 7 wherein said dopamine beta hydroxylase inhibitor compound is fusaric acid.

10. The method of claim 7 wherein said dopamine beta hydroxylase inhibitor compound is 3-phenylpropargylamine.

11. The method of claim 7 wherein said dopamine beta hydroxylase inhibitor compound is disulfiram.

12. The method of claim 7 wherein said subject is a human.

13. The method of claim 12 wherein said predetermined time is within the interval from about 07:00 h to about 13:00 h.

14. The method of claim 12 which comprises administering said dopamine beta hydroxylase inhibitor in an amount between about 1 to about 150 mg per kg of body weight per day.

15. The method of claim 12 which comprises administering multiple doses of said dopamine beta hydroxylase inhibitor within said time interval.

16. The method of claim 7 wherein said subject is a human and said dopamine beta hydroxylase inhibitor is administered for between 10 and 180 days.

* * * * *